United States Patent
Pollak et al.

[11] Patent Number: 5,976,495
[45] Date of Patent: *Nov. 2, 1999

[54] PEPTIDE DERIVED RADIONUCLIDE CHELATORS

[75] Inventors: Alfred Pollak; Anne Goodbody, both of Toronto, Canada

[73] Assignee: Resolution Pharmaceuticals, Inc., Ontario, Canada

[*] Notice: This patent is subject to a terminal disclaimer.

[21] Appl. No.: 08/612,842

[22] PCT Filed: Apr. 28, 1995

[86] PCT No.: PCT/CA95/00249

§ 371 Date: Mar. 20, 1996

§ 102(e) Date: Mar. 20, 1996

[87] PCT Pub. No.: WO96/03427

PCT Pub. Date: Feb. 8, 1996

[51] Int. Cl.[6] .......................... A61K 51/00; A61M 36/14
[52] U.S. Cl. .......................... 424/1.69; 534/14; 530/300; 530/328; 530/329; 530/330; 424/1.65; 424/1.11
[58] Field of Search .................. 424/1.11, 1.65, 424/1.69, 9.1, 9.3, 9.4, 9.5; 534/7, 10–16; 530/300; 556/1; 546/152, 184, 249, 250; 540/450; 544/63, 224; 548/100, 215, 300.1, 400

[56] References Cited

U.S. PATENT DOCUMENTS

| | | | |
|---|---|---|---|
| 5,480,970 | 1/1996 | Pollak et al. | 530/328 |
| 5,569,745 | 10/1996 | Goodbody et al. | 530/328 |
| 5,662,885 | 9/1997 | Pollak et al. | 424/1.69 |
| 5,679,642 | 10/1997 | Goodbody et al. | 514/16 |
| 5,780,006 | 7/1998 | Pollak et al. | 424/1.69 |
| 5,804,158 | 9/1998 | Pollak | 424/1.69 |

FOREIGN PATENT DOCUMENTS

| | | |
|---|---|---|
| 0 250 013 | 12/1987 | European Pat. Off. |
| 93 12819 | 4/1993 | WIPO . |

OTHER PUBLICATIONS

Journal of Nuclear Medicine, vol. 35, No. 5SUP, Jun. 1994, pp. 44P–45P, "Imaging inflammation with novel peptide Technetium–99m chelators . . . ".

Journal of Nuclear Medicine, vol. 35, No. 2, Feb. 1994, pp. 282–288, "Thrombus imaging with Technetium–99m synthetic peptides based upon . . . ".

Primary Examiner—Jose' G. Dees
Assistant Examiner—Dameron Jones
Attorney, Agent, or Firm—Nikaido Marmelstein Murray & Oram, LLP

[57] ABSTRACT

For use in imaging sites of diagnostic interest within the body, the present invention provides radionuclide chelators of formula (I), wherein X is a linear or branched, saturated or unsaturated $C_{1-4}$alkyl chain that is optionally interrupted by one or two heteroatoms selected from N, O and S; and is optionally substituted by at least one group selected from halogen, hydroxyl, amino, carboxyl $C_{1-4}$alkyl, aryl and C(O)Z; Y is H or a substituent defined by X; X and Y may together form a 5- to 8-membered saturated or unsaturated heterocyclic ring optionally substituted by at least one group selected from halogen, hydroxyl, amino, carboxyl oxo, $C_{1-4}$alkyl, aryl and C(O)Z; $R^1$ through $R^4$ are selected independently from H; carboxyl; $C_{1-4}$alkyl; $C_{1-4}$alkyl substituted with a group selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)Z; $R^5$ and $R^6$ are selected independently from H; carboxyl; amino; $C_{1-4}$alkyl; $C_{1-4}$alkyl substituted by hydroxyl, carboxyl or amino; and C(O)Z; $R^7$ is selected from H and a sulfur protecting group; and Z is selected from hydroxyl, $C_{1-4}$alkoxy and a targeting molecule.

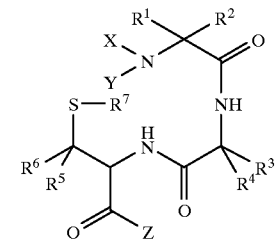

30 Claims, 1 Drawing Sheet

PEPTIDE DERIVED RADIONUCLIDE CHELATORS

This application is a 371 of PCT/CA95/00249 filed Apr. 28, 1995.

FIELD OF THE INVENTION

This invention is in the field of diagnostic imaging, and relates to chemical chelators useful in the radiolabeling of agents that target tissues of diagnostic interest.

BACKGROUND TO THE INVENTION

The art of diagnostic imaging exploits contrasting agents that in binding or localizing site selectively within the body, help to resolve the image of diagnostic interest. $^{67}$Gallium salts, for example, have an affinity for tumours and infected tissue and, with the aid of scanning tomography, can reveal afflicted body regions to the physician. Other contrasting agents include the metal radionuclides such as $^{99m}$technetium and $^{186/188}$rhenium, and these have been used to label targeting molecules, such as proteins, peptides and antibodies that localize at desired regions of the human body. As targeting agents, proteins and other macromolecules can offer the tissue specificity required for diagnostic accuracy; yet labeling of these agents with metal radionuclides is made difficult by their physical structure. Particularly, protein and peptide targeting agents present numerous sites at which radionuclide binding can occur, resulting in a product that is labeled heterogeneously. Also, and despite their possibly large size, proteins rarely present the structural configuration most appropriate for high affinity radionuclide binding, i.e. a region incorporating four or more donor atoms that form five-membered rings. As a result, radionuclides are bound typically at the more abundant low-affinity sites, forming unstable complexes.

To deal with the problem of low affinity binding, Paik et al (Nucl Med Biol 1985, 12:3) proposed a method whereby labeling of antibodies is performed in the presence of excess DPTA (diaminetrimethylenepentaacetic acid), to mask the low affinity binding sites. While the problem of low affinity binding is alleviated by this method, actual binding of the radionuclide, in this case technetium, was consequently also very low. The direct labeling of proteins having a high proportion of cysteine residues also has been demonstrated (Dean et al; WO 92/13,572). This approach exploits thiol groups of cysteine residues as high-affinity sites for radionuclide binding, and is necessarily limited in application to those targeting agents having the required thiol structure.

A promising alternative to the direct labeling of targeting agents is an indirect approach, in which targeting agent and radionuclide are coupled using a chelating agent. Candidates for use as chelators are those compounds that bind tightly to the chosen metal radionuclide and also have a reactive functional group for conjugation with the targeting molecule. For use in labeling peptide and protein-based targeting agents, the chelator is ideally also peptide-based, so that the chelator-targeting molecule conjugate can be synthesized in toto using peptide synthesis techniques. For utility in diagnostic imaging, the chelator desirably has characteristics appropriate for its in vivo use, such as blood and renal clearance and extravascular diffusibility.

SUMMARY OF THE INVENTION

The present invention provides chelators that bind diagnostically useful metal radionuclides, and can be coupled to targeting agents capable of localizing at body sites of diagnostic and therapeutic interest. The chelators of the present invention are peptide analogs designed structurally to present an $N_3S$ configuration capable of binding oxo, dioxo and nitrido ions of $^{99m}$technetium and $^{186/188}$rhenium.

More particularly, and according to one aspect of the invention, there are provided metal radionuclide chelators of the formula:

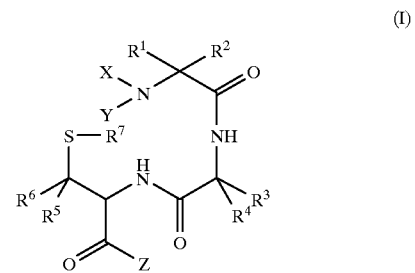

(I)

wherein

X is a linear or branched, saturated or unsaturated $C_{1-4}$alkyl chain that is optionally interrupted by one or two heteroatoms selected from N, O and S; and is optionally substituted by at least one group selected from halogen, hydroxyl, amino, carboxyl, $C_{1-4}$alkyl, aryl and C(O)Z;

Y is H or a substituent defined by X;

X and Y may together form a 5- to 8-membered saturated or unsaturated heterocyclic ring optionally substituted by at least one group selected from halogen, hydroxyl, amino, carboxyl, oxo, $C_{1-4}$alkyl, aryl and C(O)Z;

$R^1$ through $R^4$ are selected independently from H; carboxyl; $C_{1-4}$alkyl; $C_{1-4}$alkyl substituted with a group selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)Z;

$R^5$ and $R^6$ are selected independently from H; carboxyl; amino; $C_{1-4}$alkyl; $C_{1-4}$alkyl substituted by hydroxyl, carboxyl or amino; and C(O)Z;

$R^7$ is selected from H and a sulfur protecting group; and

Z is selected from hydroxyl, $C_{1-4}$alkoxy and a targeting molecule.

According to another aspect of the invention, the chelators of the invention are provided in a form having a metal radionuclide complexed therewith having the general formula:

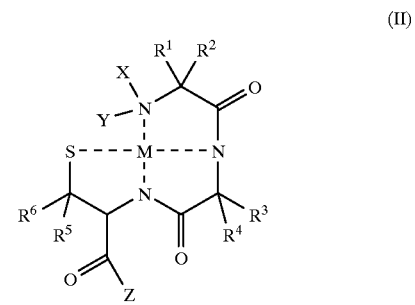

(II)

wherein

X is a linear or branched, saturated or unsaturated $C_{1-4}$alkyl chain that is optionally interrupted by one or two heteroatoms selected from N, O and S; and is optionally substituted by at least one group selected from halogen, hydroxyl, amino, carboxyl, $C_{1-4}$alkyl, aryl and C(O)Z;

Y is H or a substituent defined by X;

X and Y may together form a 5- to 8-membered saturated or unsaturated heterocyclic ring optionally substituted by at least one group selected from halogen, hydroxyl, amino, carboxyl, oxo, $C_{1-4}$alkyl, aryl and C(O)Z;

$R^1$ through $R^4$ are selected independently from H; carboxyl; $C_{1-4}$alkyl; $C_{1-4}$alkyl substituted with a group selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)Z;

$R^5$ and $R^6$ are selected independently from H; carboxyl; amino; $C_{1-4}$alkyl; $C_{1-4}$alkyl substituted by hydroxyl, carboxyl or amino; and C(O)Z;

Z is selected from hydroxyl, $C_{1-4}$alkoxy and a targeting molecule; and

M is a metal radionuclide or an oxide or nitride thereof.

In another aspect of the invention, there is provided a conjugate in which the chelator is provided in a form coupled to a diagnostically useful targeting molecule, and optionally in combination with a complexed metal radionuclide, for imaging use.

In another aspect of the invention, there is provided a method of imaging sites of diagnostic interest in which a conjugate of the invention is first administered as a radionuclide complex to a patient; and then the location of the radionuclide is detected using imaging means.

DETAILED DESCRIPTION OF THE INVENTION

Figure 1:
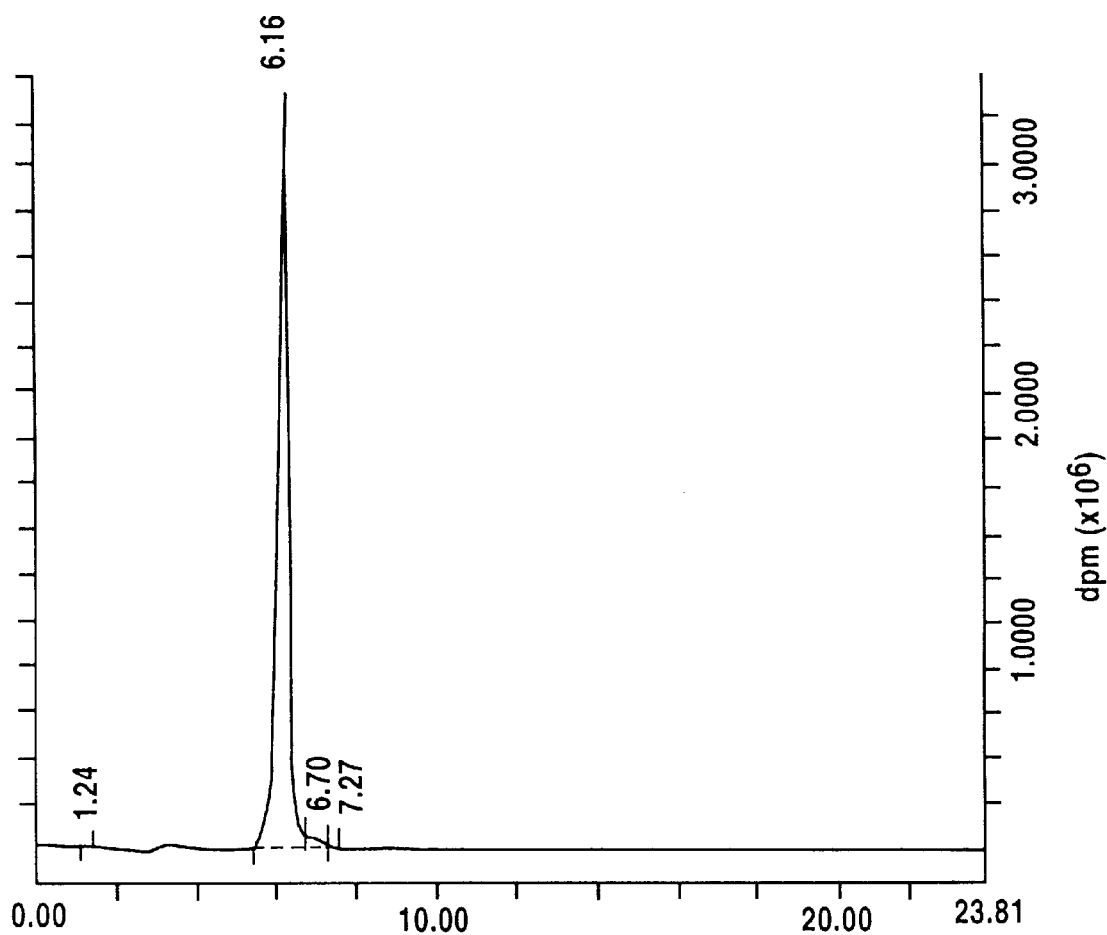
FIG. 1 is an HPLC analysis of conjugate N,N-dimethylGly-Ser-Cys(Acm)-Gly-Thr-Lys-Pro-Pro-Arg-OH (SEQ ID NO: 1) labeled with $^{99m}$Tc.

The invention provides metal radionuclide chelators that when coupled to a targeting molecule are useful for delivering a radionuclide to a body site of therapeutic or diagnostic interest. As illustrated in the above formula, the chelators are peptidic compounds that present an $N_3S$ configuration in which the radionuclide is complexed.

Terms defining the variables $R^1$–$R^7$, X, Y and Z as used hereinabove have the following meanings:

"alkyl" refers to a straight or branched $C_{1-4}$ chain;

"aryl" refers to aromatic and heteroaromatic rings;

"halogen" refers to F, Cl and Br;

"sulfur protecting group" refers to a chemical group that inhibits oxidation of a thiol group, which includes those that are cleaved upon chelation of the metal. Suitable sulfur protecting groups include known alkyl, aryl, acyl, alkanoyl, aryloyl, mercaptoacyl and organothio groups.

In preferred embodiments of the invention, the chelators conform to the above formula in which:

$R^1$ through $R^4$ are selected independently from H; and a hydroxy-substituted $C_{1-4}$alkyl group such as hydroxymethyl and 1-hydroxyethyl;

$R^5$ and $R^6$ are selected independently from H and $C_{1-4}$alkyl, and are preferably both H;

$R^7$ is a hydrogen atom or a sulfur protecting group and is most preferably acetamidomethyl;

X is a $C_{1-4}$alkyl chain, preferably methyl or ethyl; or is a $C_{1-4}$alkyl chain substituted with an aryl group, preferably to form a benzyl group;

Y is H or a substituent defined by X; and is preferably methyl, ethyl or benzyl and most preferably is the same as X;

Z is OH, $C_{1-4}$alkoxy or a targeting molecule, and is preferably a peptide targeting molecule.

Specific chelators of the invention include:

N,N-dimethylGly-Ser-Cys(Acm)-OH;

N,N-dimethylGly-Thr-Cys(Acm)-OH:

N,N-diethylGly-Ser-Cys(Acm)-OH;

N,N-dibenzylGly-Ser-Cys(Acm)-OH; and

Sarcosine-Ser-Cys(Acm)-OH.

In the case where the substituents represented by X and Y together with the adjacent nitrogen atom form a hetero ring, such a ring may be a 5- to 8-membered, saturated ring, for example pyrrolidine, piperidine, 1-azacycloheptane and 1-azacyclooctane. Unsaturated rings formed by X and Y include pyrrole and 4H-pyridine while it is understood that the coordinating nitrogen of the ring is necessarily trivalent and cannot form a double bond to an adjacent atom. The heterocycle formed by X and Y may also incorporate one or two additional heteroatoms selected from N, O and S. Rings having additional heteroatoms include but are not limited to 1-imidazole, pyrazole, piperazine, morpholine and thiomorpholine. The ring formed by X and Y may also be substituted with one or more and preferably less than three groups selected from halogen, hydroxyl, carboxyl, oxo, $C_{1-4}$alkyl and aryl, for example to form 4-oxo-1-piperidine, 4oxo-1-pyrrolidine and 4hydroxy-1-piperidine.

For diagnostic imaging purposes, the chelator pre se may be used in a form complexed with a metal radionuclide. Suitable radionuclides include $^{99m}$Tc, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{212}$Pb and $^{212}$Bi in their various oxides or nitrides. Preferred metal radionuclides are technetium ($^{99m}$Tc) and rhenium ($^{186, 188}$Re) in their oxide forms such as $ReO^{3+}$, $ReO_2^+$, $^{99m}TcO_2^+$ and most preferably $^{99m}TcO^{3+}$. Desirably and according to a preferred aspect of the invention, the chelator is coupled to a targeting molecule represented by Z in the above formula, to form a conjugate that serves to deliver a chelated radionuclide to a desired location in a mammal. Examples of targeting molecules suitable for coupling to the chelator include, but are not limited to, steroids, proteins, peptides, antibodies, nucleotides and saccharides. Preferred targeting molecules include proteins and peptides, particularly those capable of binding with specificity to cell surface receptors characteristic of a particular pathology. For instance, disease states associated with over-expression of particular protein receptors can be imaged by labeling that protein or a receptor binding fragment thereof coupled to a chelator of invention. Most preferably targeting molecules are peptides capable of specifically binding to target sites and have three or more amino acid residues. Targeting peptides useful to image certain medical conditions and tissues are noted below: for atherosclerotic plaque:

| | | | |
|---|---|---|---|
| YRALVDTLK | (SEQ ID NO:2) | RALVDTLK | (SEQ ID NO:3) |
| RALVDTLKFVTQAEGAK | (SEQ ID NO:4) | YAKFRETLEDTRDRMY | (SEQ ID NO:5) |
| AKFRETLEDTRDRMY | (SEQ ID NO:6) | AALDLNAVANKIADFEL | (SEQ ID NO:7) |
| YAALDLNAVANKIADFEL | (SEQ ID NO:8) | YRALVDTLKFVTEQAKGA | (SEQ ID NO:9) |
| RALVDTLKFVTEQAKGA | (SEQ ID NO:10) | YRALVDTEFKVKQEAGAK | (SEQ ID NO:11) |
| RALVDTEFKVKQEAGAK | (SEQ ID NO:12) | YRALVDTLKFVTQAEGAK | (SEQ ID NO:13) | for infections and atherosclerotic plaque:

| | | | |
|---|---|---|---|
| VGVAPGVGVAPGVGVAPG | (SEQ ID NO:14) | formyl.NIeu.LF.NIeu.YK | (SEQ ID NO:15) |
| VPGVGVPGVGVPGVGVPGVG | (SEQ ID NO:16) | formyIMIFL | (SEQ ID NO:17) |
| formyIMLFK | (SEQ ID NO:18) | formyIMLFI | (SEQ ID NO:19) |
| formyIMFIL | (SEQ ID NO:20) | formyIMFLI | (SEQ ID NO:21) |
| formyIMLIF | (SEQ ID NO:22) | formyIMILF | (SEQ ID NO:23) |
| formyITKPR | (SEQ ID NO:24) | VGVAPG | (SEQ ID NO:25) |
| formyIMLF | | YIGSR | (SEQ ID NO:26) |
| CH$_2$CO.YIGSRC | (SEQ ID NO:27) | | | for thrombus:

| | | | |
|---|---|---|---|
| NDGDFEEIPEEYLQ | (SEQ ID NO:28) | NDGDFEEIPEEY(SO$_3$Na)LQ | (SEQ ID NO:29) |
| GPRG | (SEQ ID NO:30) | | | for platelets:

| | | | |
|---|---|---|---|
| D-Phe.PRPGGGGNGDFEEIPEEYL | (SEQ ID NO:31) | RRRRRRRRGDV | (SEQ ID NO:32) |
| PLYKKIIKKLLES | (SEQ ID NO:33) | RGD | |
| RGDS | (SEQ ID NO:34) | | | for amyloid plaque (Alzheimer's disease):

| | |
|---|---|
| EKPLQNFTLSFR | (SEQ ID NO:35) |

For connection to the chelator, a targeting molecule may comprise a "spacer" that serves to create a physical separation between the chelator and the targeting molecule. A spacer may be an alkyl chain that is derivatized for coupling to the chelator. In the case where the targeting molecule is a peptide, the spacer may suitably be one or more amino acid residues. Preferably, peptidic targeting molecules incorporate spacers of from 1 to 5 amino acids such having chemically inert α-carbon side chains, such as glycine or β-alanine residues.

A targeting molecule may be coupled to a chelator of the invention at various sites including $R^1$ to $R^6$, X, Y and Z as well as a ring formed by X and Y. Coupling may be achieved by reacting a group present on the targeting molecule that is reactive with a substituent on the chelator to form a linkage. For example, peptide targeting molecules having a free amino group, such as an N-terminus or an ε-amino-lysine group may be reacted with a carboxyl group on the chelator to form an amide linkage. Alternatively, the C-terminus of the peptide targeting molecule may be reacted with an amino substituent on the chelator. In a preferred embodiment, targeting molecules are coupled to chelators of formula (I) at substituent Z by an amide linkage such as a peptide bond. For example, the N-terminus amino group of a peptide targeting molecule is reacted with a carboxyl group at Z. Targeting molecules other than peptides may be coupled to chelators of the invention in a similar manner provided that a group suitable for coupling to the chelator is present. In the instance that a suitable group is not present, the targeting molecule may be chemically derivatized to present such a group. When more than one reactive group is present on the chelator or targeting molecule, it is desirable to block all but the particular group for coupling with an appropriate blocking agent in order to achieve a single conjugate species. For example, free carboxyl groups may be protected by forming esters such as a t-butyl ester which can be removed with TFA. Free amino groups may be protected with a blocking group such as FMOC which may be subsequently removed with piperidine.

In a particular embodiment of the invention, imaging in vivo sites of focal inflammation is accomplished using a conjugate in which the targeting molecule is a chemotactic peptide comprising the amino acid sequence Thr-Lys-Pro-Pro-Lys (TKPPR) (SEQ ID NO: 36). It has been found that this peptide binds particularly well to leukocytes receptors. Targeting peptides can be spaced from the chelator by additional amino acid residues, preferably glycine, provided the peptide retains its localizing activity. In a particular embodiment, the peptide TKPPR (SEQ ID NO: 36) is coupled to substituent Z of chelators according to formula (I) by a Gly residue.

Peptide-based targeting molecules can be made, either per se or as a conjugate with a chelator, using various established techniques. Because it is amenable to solid phase synthesis, employing alternating FMOC protection and deprotection is the preferred method of making short peptides. Recombinant DNA technology is preferred for producing proteins and long fragments thereof. In a particular embodiment, peptide-chelator conjugates are prepared by solid-phase peptide synthesis methods, which involve the stepwise addition of amino acid residues to a growing peptide chain that is linked to an insoluble (solid) support or matrix, such as polystyrene. The C-terminal residue of the targeting peptide is first anchored to a commercially available support with its amino group protected with an N-protecting agent such as a fluorenylmethoxycarbonyl (FMOC) group. Typically, the support is obtained with the C-terminal residue preloaded in protected form. The amino protecting group is removed with suitable deprotecting agents such as piperidine and the next amino acid residue (in N-protected form) is added with a coupling agent such as dicyclocarbodiimide (DCC). Upon formation of a peptide bond, the reagents are washed from the support. Once the targeting peptide chain is synthesized, the first residue of the chelator ie. S-acetamidomethyl protected cysteine is added to the N-terminus. The final residue of the chelator is a derivatized amino acid residue that conforms to the formula $(X)(Y)N-C(R^1)(R^2)-CO-$ wherein X, Y, $R^1$ and $R^2$ have the meaning previously defined. The final residue, for example dimethyl-glycine, diethyl-glycine, dibenzyl-glycine or sarcosine, may be commercially obtained or synthesized. The completed conjugate is cleaved from the support with a suitable reagent such as trifluoroacetic acid (TFA).

It will be appreciated that all substituents $R^1$ through $R^4$ according to the invention are side chains of naturally occurring or derivatized amino acids including D-amino acids and are commercially available and compatible with solid phase synthesis techniques. Derivatized amino acid residues that are not commercially available may be incorporated in chelators of the invention by synthesizing them according to established organic chemistry techniques and inserting at the appropriate stage of solid phase peptide synthesis previously described. Similarly when substituents $R^5$ and $R^6$ are other than H, a derivatized cysteine amino acid residue is utilized in the peptide synthesis. For example, the commercially available residue penecillamine is incorporated when $R^5$ and $R^6$ are both methyl.

Various substituents at X and Y may be introduced in chelators of the invention by incorporating as the final residue of solid phase synthesis a derivatized amino acid according to the formula $(X)(Y)N-C(R^1)(R^2)-C(O)-OH$ wherein X, Y, $R^1$ and $R^2$ have the meaning previously described. Amino acids having N-terminal amino substituents according to X and Y may be synthesized according to established organic chemistry procedures and techniques. For example, when X and Y are both dibenzyl substituents the corresponding dibenzylglycine residue may be synthesized by reacting commercially available reagents bromoacetic acid and dibenzylamine in a suitable solvent such as dichloromethane and then heating. Other amines may be employed in the reaction in place of dibenzylamine such as diisopropylamine to give the corresponding diisopropylglycine. Similarly cyclic amines such as piperidine and morpholine in place of dibenzylamine will give the corresponding piperidyl-glycine and morpholinyl-glycine residues.

In a most preferred embodiment of the invention a peptide-chelator conjugate is prepared on a solid support and has the structure of formula (I) wherein the targeting molecule is a peptide having a sequence Gly-Thr-Lys-Pro-Pro-Arg-OH (SEQ ID NO: 37); $R^1$, $R^2$, $R^3$, $R^5$ and $R^6$ are H; $R^4$ is hydroxymethyl or 1-hydroxyethyl and $R^7$ is acetamidomethyl.

Incorporation of the selected radionuclide within the chelator can be achieved by various established methods. For example the following general procedure may be used. A chelator solution is formed initially by dissolving the chelator in aqueous alcohol eg. ethanol-water 1:1. Oxygen is removed for example by degassing with $N_2$, then sodium hydroxide is added to remove the thiol protecting group. The solution is again purged of oxygen and heated on a water bath to hydrolyze the thiol protecting group, and the solution is then neutralized with an organic acid such as acetic acid (pH 6.0–6.5). In the labeling step, sodium pertechnetate is added to a chelator solution with an amount of stannous chloride sufficient to reduce the technetium. The solution is mixed and left to react at room temperature and then heated on a water bath. In an alternative method, labeling can be accomplished with the chelator solution adjusted to pH 8. At this higher pH, pertechnetate may be replaced with a solution containing technetium complexed with labile ligands suitable for ligand exchange reactions with the desired chelator. Suitable ligands include tartarate, citrate and heptagluconate. Stannous chloride may be replaced with sodium dithionite as the reducing agent if the chelating solution is alternatively adjusted to a still higher pH of 12–13 for the labeling step. The chelators of the present invention can be coupled to a targeting molecule prior to labeling with the radionuclide, a process referred to as the "bifunctional chelate" method. An alternative approach is the "prelabeled ligand" method in which the chelator is first labeled with a radionuclide and is then coupled to the targeting molecule.

The labeled chelator may be separated from contaminants $^{99m}TcO_4^-$ and colloidal $^{99m}TcO_2$ chromatographically, e.g., with a C-18 Sep Pak column activated with ethanol followed by dilute HCl. Eluting with dilute HCl separates the $^{99m}TcO_4^-$, and eluting with EtOH-saline 1:1 brings off the chelator while colloidal $^{99m}TcO_2$ remains on the column.

When coupled to a targeting molecule and labeled with a diagnostically useful metal, chelators of the present invention can be used to detect pathological conditions by techniques common in the art of diagnostic imaging. A chelator-targeting molecule conjugate labeled with a radionuclide metal such as technetium may be administered to a mammal intralymphatically, intraperitoneally and preferably intravenously in a pharmaceutically acceptable solution such as saline or blood plasma medium. The amount of labeled conjugate administered is dependent upon the toxicity profile of the chosen targeting molecule as well as the profile of the metal and is typically in the range of about 0.01 to 100 and preferably 10 to 50 mCi per 70 Kg host. Localization of the metal in vivo is tracked by standard scintigraphic techniques at an appropriate time subsequent to its administration. The time at which an image may be obtained will depend upon the profile of the targeting molecule, for example most peptides will localize rapidly allowing for an image to be obtained within 3 hours and often within 1 hour. In a particular embodiment, chelators of the invention coupled to a peptide targeting molecule GTKPPR (SEQ ID NO: 37) in a saline solution are administered by intravenous injection to image sites of focal inflammation.

The following examples are presented to illustrate certain embodiments of the present invention.

EXAMPLE 1

Preparation of Peptide-Chelator Conjugates

N,N-dimethylGly-Ser-Cys(Acm)-Gly-Thr-Lys-Pro-Pro-Arg (SEQ ID NO: 1)
N,N-dimethylGly-Thr-Cys(Acm)-Gly-Thr-Lys-Pro-Pro-Arg (SEQ ID NO: 38) and
Sarcosine-Gly-Ser-Cys(Acm)-Gly-Thr-Lys-Pro-Pro-Arg (SEQ ID NO: 1)

The title conjugates were prepared as a single peptide chain by solid phase peptide synthesis using FMOC chemistry on an FMOC-arginine preloaded 2-methoxy-4-alkoxybenzyl alcohol resin (Sasrin Resin, Bachem Biosciences In., Philadelphia) with an Applied Biosystems 433A peptide synthesizer (Foster City, Calif.). Derivatized amino acid residues S-acetamidomethyl-cysteine (Bachem), N,N-dimethylglycine (Sigma Chemical Company, St. Louis, Mo.), and sarcosine were incorporated at the appropriate step of chain elongation.

Upon addition of the final residue N,N-dimethylGly or Sarcosine, the peptide-resin was dried under vacuum overnight and cleavage of the peptide from the resin was achieved by mixing a cooled solution of 9.5 mL trifluoroacetic acid (TFA), 0.5 mL water, 0.5 mL thioanisole and 0.25 mL 2-ethanedithiol (1 mL per 100 mg of peptide-resin) with the peptide-resin for 1.5 to 2 hours at room temperature. The resin was removed by filtration and washed with 1–3 mL of TFA to obtain 6–8 mL of a clear yellow liquid. This liquid was slowly dropped into 30–35 mL of cold tert-butyl ether in a 50 mL conical polypropylene centrifuge tube forming a white precipitate. The precipitate was centrifuged at 7000 rpm, 0° C. for 5 minutes (Sorvall RT6000, Dupont), decanted and washed two more times with tert-butyl ether. Following drying under vacuum the precipitate was dissolved in water. The solution was frozen in acetone-dry ice and lyophilized overnight. The resulting white powder was dissolved in water, filtered through a 0.45 µm syringe filter (Gelman Acrodisc 3 CR PTFE), and purified by reversed-phase HPLC (Beckman System Gold) with a C18 column (Waters RCM 25×10) using 1% TFA in water as buffer A and 1% TFA in acetonitrile as buffer B. The column was equilibrated with 100:0 buffer A:buffer B and eluted with a linear gradient in 25 minutes at 1 mL/min to 50% buffer B. Fractions were reanalysed on the HPLC and pooled according to matching profiles. The pure fractions were frozen in acetone-dry ice and lyophilized 12 hours to give a white powder.

EXAMPLE 2

Preparation of Peptide-Chelator Conjugate

N,N-dibenzylGly-Ser-Cys(Acm)-Gly-Thr-Lys-Pro-Pro-Arg (SEQ ID NO: 1)
N,N-diethylGly-Ser-Cys(Acm)-Gly-Thr-Lys-Pro-Pro-Arg (SEQ ID NO: 1)

The title conjugate was prepared as a single peptide chain by solid phase peptide synthesis using FMOC chemistry on an FMOC-arginine preloaded 2-methoxy-4-alkoxybenzyl alcohol resin (Sasrin Resin, Bachem Biosciences In., Philadelphia) with an Applied Biosystems 433A peptide synthesizer (Foster City, Calif.). Derivatized amino acid residues S-acetamidomethyl-cysteine (Bachem) N,N-diethylglycine and N,N-dibenzylglycine were incorporated at the appropriate step of chain elongation.

The derivatized amino acid residue N,N-dibenzylglycine was synthesized by the following procedure:

In a flask equipped with magnetic stir, bromoacetic acid (5.00 g, 35.99 mmol) was dissolved in $CH_2Cl_2$, cooled to 0° C. and dibenzylamine (8.31 mL, 43.79 mmol) was added. The reaction mixture was stirred at 0° C. for 1 h and allowed to warm to room temperature and then heated to between 30–40° C. for 12 hours. The mixture solution was cooled to room temperature and $CH_2Cl_2$ was evaporated under reduced pressure, then washed with hot ethanol and dried under vacuum giving a white solid residue (71.2% yield).

The derivatized amino acid residue N,N-diethylglycine was synthesized by the following procedure:

In a flask, chloroacetic acid (5.00 g, 52.91 mmol) was added to diethylamine (35 mL) and stirred for 12 hours at room temperature then heated at reflux for 72 hours. The reaction mixture was cooled to room temperature and neutralized with HCl and concentrated to reduced volume. Ethylacetate and EtOH were then added and the resulting white precipitate was filtered and dried under vacuum to give 1.74 g (25% yield) of the product.

EXAMPLE 3

Labeling of Peptide-Chelator Conjugates

N,N-dimethylGly-Ser-Cys(Acm)-GTKPPR (SEQ ID NO: 1)
N,N-dimethylGly-Thr-Cys(Acm)-GTKPPR (SEQ ID NO: 38)
N,N-diethylGly-Ser-Cys(Acm)-GTKPPR (SEQ ID NO: 1)
N,N-dibenzylGly-Ser-Cys(Acm)-GTKPPR (SEQ ID NO: 1) and
Sarcosine-Ser-Cys(Acm)-GTKPPR (SEQ ID NO: 39)

The conjugates of examples 1 and 2 were reconstituted (200 µL, 1 mg/mL saline) and then injected into 3 mL vacutainers with 100 µL pertechnetate (10 mCi) and 100 µL stannous gluconate (50 µg stannous chloride and 1 mg sodium gluconate). The tubes were placed in boiling water bath for 12 minutes and then filtered through a Whatman PVDF syringe filter to collect the labeled conjugate solutions which were further diluted with saline to prepare injectable solutions (2 Mbq/mL). The conjugates were isolated by HPLC (Beckman) from a (20 µL) sample (before dilution) to determine the labeling yield by measuring radioactivity.

| conjugate | | labelling yield |
|---|---|---|
| N,N-dimethylGly-Ser-Cys(Acm)-GTKPPR | (SEQ ID NO:1) | >94% |
| N,N-dimethylGly-Thr-Cys(Acm)-GTKPPR | (SEQ ID NO:38) | >94% |
| N,N-diethylGly-Ser-Cys(Acm)-GTKPPR | (SEQ ID NO:1) | 85.4% |
| N,N-dibenzylGly-Ser-Cys(Acm)-GTKPPR | (SEQ ID NO:1) | 98.9% |
| Sarcosine-Ser-Cys(Acm)-GTKPPR | (SEQ ID NO:39) | 90.3% |

Each conjugate except Sarcosine-Ser-Cys(Acm)-GTKPPR (SEQ ID NO: 39) gave a single peak and greater than 85% labeling yield. 24 hours after labeling, N,N-dimethylGly-Ser-Cys(Acm)-Gly-Thr-Lys-Pro-Pro-Arg (SEQ ID NO: 1) was reanalyzed on HPLC and observed to have no degradation or radiolysis products.

EXAMPLE 4

In vivo Imaging and Biodistribution of Conjugates

Rat inflammation studies were performed as follows. 2 male Wistar rats (Charles River, 200–250 g) were injected intramuscularly with (25 mg) zymosan, a yeast cell wall suspension, into their left hindlegs 24 hours before imaging. Focal inflammation in the leg was visually detectable after 1 day. 1 mg (ca. 0.7 $\mu$Mol) of the chelator-peptide conjugate was dissolved in 50 $\mu$L of dimethylsulfoxide and added to an ethanol-water mixture (1:1, 200 $\mu$L). An aliquot of Tc-99m tartarate (ca. 400 MBq) was added and transchelation allowed to proceed for 20 min. at 100° C. The Tc-99m labeled conjugate was purified by elution through a Sep Pak cartridge and then diluted with saline to prepare an injectable formulation (200 $\mu$L) containing about 100 $\mu$Ci (3.7 MBq) of activity.

The rats were anaesthetized with somnitol (40 to 50 mg/kg), and the labeled conjugate solution (200 $\mu$L) was injected intravenously via the tail vein. Serial whole-body scintigrams were acquired at 30 minutes. The rats were then killed with anaesthesia overdose and samples of organs, urine, blood, inflamed muscle (left leg) and non-inflamed muscle (right leg) and inflammatory exudate (fluid) were weighed and counted in either a well-type gamma counter or in a gamma dose calibrator depending upon the organ. The dose calculations were made based on the assumption that the blood volume constituted 8% of body weight. The results of the conjugates represented in the table below are averages for two rats and are corrected for the residual dose in the tail.

Both conjugates gave excellent scintigraphic images in comparison to other known inflammation imaging agents such as Ga-67, $^{99m}$Tc-IgG, $^{111}$In-WBC and $^{99m}$Tc-Nanocoll which is indicated by the high target to background ratios (inflamed:uninflamed muscle) observed. The conjugates imaged much more rapidly than the known agents and exhibited superior biodistribution. Also, non-target organs such as liver and GI tract showed low accumulation.

| Imaging Agent | Inflam: Uninfl | Fluid: Blood | Urine (% dose) | Liver (% dose) | GI Tract (% dose) |
|---|---|---|---|---|---|
| N,N-dimethylGly—Ser—Cys(Acm)—GTKPPR—OH (SEQ ID NO: 1) | 5.3 | 1.9 | 63.5 | 2.4 | 2.8 |
| N,N-dimethylGly—Thr—Cys(Acm)—GTKPPR—OH (SEQ ID NO: 38) | 4.6 | 1.6 | 68.5 | 2.4 | 2.5 |
| N,N-dibenzylGly—Ser—Cys(Acm)—GTKPPR—OH (SEQ ID NO: 1) | 3.7 | 0.4 | 55.1 | 2.3 | 7.5 |
| $^{67}$Ga | 2.5 | 0.1 | 5.5 | 26.5 | 8.4 |
| $^{99m}$Tc—IgG | 2.8 | 0.03 | 1.2 | 17.6 | 0.7 |
| $^{111}$In—WBC | 1.5 | 0.1 | 0.2 | 36.9 | 3.6 |
| $^{98m}$Tc-Nanocoll | 3.3 | 0.2 | 0.8 | 66.7 | 2.1 |

We claim:

1. A compound of the general formula:

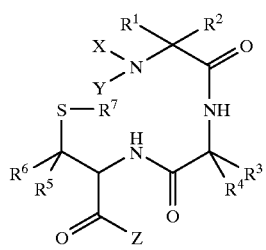

(I)

wherein

X is a linear or branched, saturated or unsaturated $C_{1-4}$alkyl chain that is optionally interrupted by one or two heteroatoms selected from N, O and S; and is optionally substituted by at least one group selected from halogen, hydroxyl, amino, carboxyl, $C_{1-4}$alkyl, aryl and C(O)Z;

Y is H or a substituent defined by X:

X and Y may together form a 5- to 8-membered saturated or unsaturated heterocyclic ring optionally substituted by at least one group selected from halogen, hydroxyl, amino, carboxyl, oxo, $C_{1-4}$alkyl, aryl and C(O)Z;

$R^1$ through $R^4$ are selected independently from H; carboxyl; $C_{1-4}$alkyl; $C_{1-4}$alkyl substituted with a group selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)Z;

$R^5$ and $R^8$ are selected independently from H; carboxyl; amino; $C_{1-4}$alkyl; $C_{1-4}$alkyl substituted by hydroxyl, carboxyl or amino; and C(O)Z;

$R^7$ is selected from H and a sulfur protecting group; and

Z is selected from hydroxyl, $C_{1-4}$alkoxy and a targeting molecule.

2. A compound according to claim 1, wherein $R^1$, $R^2$, $R^4$, $R^5$ and $R^6$ are hydrogen.

3. A compound according to claim 1, wherein X and Y are independently selected from $C_{1-4}$alkyl and aryl substituted $C_{1-4}$alkyl.

4. A compound according to claim 1, wherein $R^3$ is selected from hydroxymethyl and 1-hydroxyethyl.

5. A compound according to claim 1, wherein Y is independently a substituent defined by X.

6. A compound according to claim 5, wherein X and Y are the same group selected from methyl, ethyl and benzyl.

7. A compound according to claim 5, wherein $R^3$ is selected from hydroxymethyl and 1-hydroxyethyl.

8. A compound according to claim 5, wherein $R^1$, $R^2$, $R^4$, $R^5$ and $R^6$ are hydrogen.

9. A compound according to claim 1, wherein Z is a targeting molecule.

10. A compound according to claim 9, wherein the targeting molecule is a peptide.

11. A compound according to claim 10, wherein the peptide comprises 3 or more amino acid residues.

12. A compound according to claim 11, wherein the peptide comprises the sequence TKPPR (SEQ ID NO: 36).

13. A compound according to claim 12, wherein the peptide comprises the sequence Gly-Thr-Lys-Pro-Pro-Arg-OH (SEQ ID NO: 37).

14. A compound according to claim 1, in a form complexed with a metal radionuclide or an oxide or nitride thereof.

15. A compound according to claim 14, wherein said metal radionuclide is selected from $^{99m}$Tc, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{212}$Pb and $^{212}$Bi.

16. A compound according to claim 14, wherein said metal radionuclide is selected from $^{99m}$Tc, $^{186}$Re and $^{188}$Re.

17. A compound according to claim 14, wherein said metal radionuclide is $^{99m}$Tc.

18. A compound of the general formula:

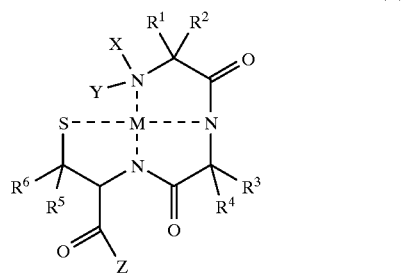

(II)

wherein
- X is a linear or branched, saturated or unsaturated $C_{1-4}$alkyl chain that is optionally interrupted by one or two heteroatoms selected from N, O and S; and is optionally substituted by at least one group selected from halogen, hydroxyl, amino, carboxyl, $C_{1-4}$alkyl, aryl and C(O)Z;
- Y is H or a substituent defined by X;
- X and Y may together form a 5- to 8-membered saturated or unsaturated heterocyclic ring optionally substituted by at least one group selected from halogen, hydroxyl, amino, carboxyl, oxo, $C_{1-4}$alkyl, aryl and C(O)Z;
- $R^1$ through $R^4$ are selected independently from H; carboxyl; $C_{1-4}$alkyl; $C_{1-4}$alkyl substituted with a group selected from hydroxyl, amino, sulfhydryl, halogen, carboxyl, $C_{1-4}$alkoxycarbonyl and aminocarbonyl; an alpha carbon side chain of a D- or L-amino acid other than proline; and C(O)Z;
- $R^5$ and $R^6$ are selected independently from H; carboxyl; amino; $C_{1-4}$alkyl; $C_{1-4}$alkyl substituted by hydroxyl, carboxyl or amino; and C(O)Z;
- Z is selected from hydroxyl, $C_{1-4}$alkoxy and a targeting molecule; and
- M is a metal radionuclide or an oxide or nitride thereof.

19. A compound according to claim 18, wherein M is selected from $^{99m}$Tc, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{212}$Pb and $^{212}$Bi and oxides or nitrides thereof.

20. A compound according to claim 18, wherein M is selected from $^{99m}$Tc, $^{186}$Re and $^{188}$Re and oxides or nitrides thereof.

21. A compound according to claim 18, wherein M is $^{99m}$Tc or oxides or nitrides thereof.

22. A method of detecting the localization of a targeting molecule within a mammal comprising the step of administering a diagnostically effective amount of a compound according to claim 14, wherein Z is the targeting molecule.

23. The method according to claim 22, wherein said metal radionuclide is $^{99m}$Tc.

24. A method of imaging a site of focal inflammation within a mammal comprising the step of administering a diagnostically effective amount of a compound according to claim 10, in a form complexed with a metal radionuclide or an oxide or nitride thereof.

25. The method according to claim 24, wherein said metal radionuclide is $^{99m}$Tc.

26. A method of imaging a site of focal inflammation within a mammal comprising the step of administering an effective amount of a compound according to claim 12, in a form complexed with a metal radionuclide or an oxide or nitride thereof.

27. The method according to claim 26, wherein said metal radionuclide is $^{99m}$Tc.

28. A compound according to claim 1, selected from
- N,N-dimethyl Gly-Ser-Cys(Acm)-Gly-Thr-Lys-Pro-Pro-Arg-OH (SEQ ID NO: 1);
- N,N-dimethylGly-Thr-Cys(Acm)-Gly-Thr-Lys-Pro-Pro-Arg-OH (SEQ ID NO 38);
- N,N-diethylGly-Ser-Cys(Acm)-Gly-Thr-Lys-Pro-Pro-Arg-OH (SEQ ID NO: 1); and
- N,N-dibenzylGly-Ser-Cys(Acm)-Gly-Thr-Lys-Pro-Pro-Arg-OH (SEQ ID NO: 1).

29. The compound according to claim 28, in a form complexed with a metal radionuclide or an oxide or nitride thereof.

30. The compound according to claim 29, wherein said metal radionuclide is $^{99m}$Tc.

* * * * *

Adverse Decision In Interference

Patent No. 5,976,495, Alfred Pollak, Anne Goodbody, PEPTIDE DERIVED RADIONUCLIDE CHELATORS, Interference No. 104,789, final judgment adverse to the patentees rendered April 8, 2004, as to claims 1-3, 5-6, 8-11, and 14-25.

*(Official Gazette October 12, 2004)*

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
　　　　(A) LENGTH: 9 amino acids
　　　　(B) TYPE: amino acid
　　　　(C) STRANDEDNESS: single
　　　　(D) TOPOLOGY: linear (ii) MOLECULE TYPE: peptide

```
    (ix) FEATURE:
         (A) NAME/KEY: Modified-site
         (B) LOCATION: 1
         (D) OTHER INFORMATION: /note= "Position 1 has either an
             N,N-dimethyl, an N,N-dibenzyl, an N,N-diethyl, or a
             sarcosine substituent."

(ix) FEATURE:
         (A) NAME/KEY: Modified-site
         (B) LOCATION: 9
         (D) OTHER INFORMATION: /note= "Position 9 is either
             unsubstituted or has an -OH substituent."

(xi) SEQUENCE DESCRIPTION: SEQ ID NO:1:

Gly Ser Cys Gly Thr Lys Pro Pro Arg
    1               5

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Tyr Arg Ala Leu Val Asp Thr Leu Lys
    1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Arg Ala Leu Val Asp Thr Leu Lys
    1               5

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Arg Ala Leu Val Asp Thr Leu Lys Phe Val Thr Gln Ala Glu Gly Ala
    1               5                  10                  15

Lys (2) INFORMATION FOR SEQ ID NO:5:

(i) SEQUENCE CHARACTERISTICS:
        (A) LENGTH: 16 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:5:

Tyr Ala Lys Phe Arg Glu Thr Leu Glu Asp Thr Arg Asp Arg Met Tyr
     1               5                   10                  15

(2) INFORMATION FOR SEQ ID NO:6:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:6:

Ala Lys Phe Arg Glu Thr Leu Glu Asp Thr Arg Asp Arg Met Tyr
     1               5                   10                  15

(2) INFORMATION FOR SEQ ID NO:7:

(i) SEQUENCE CHARACTERISTICS:
          (A) LENGTH: 17 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:7:

Ala Ala Leu Asp Leu Asn Ala Val Ala Asn Lys Ile Ala Asp Phe Glu
     1               5                   10                  15

Leu (2) INFORMATION FOR SEQ ID NO:8:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:8:

Tyr Ala Ala Leu Asp Leu Asn Ala Val Ala Asn Lys Ile Ala Asp Phe
     1               5                   10                  15

Glu Leu (2) INFORMATION FOR SEQ ID NO:9:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:9:

Tyr Arg Ala Leu Val Asp Thr Leu Lys Phe Val Thr Glu Gln Ala Lys
     1               5                   10                  15

Gly Ala (2) INFORMATION FOR SEQ ID NO:10:

```
    (i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Arg Ala Leu Val Asp Thr Leu Lys Phe Val Thr Glu Gln Ala Lys Gly
   1               5                  10                  15

Ala (2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Tyr Arg Ala Leu Val Asp Thr Glu Phe Lys Val Lys Gln Glu Ala Gly
   1               5                  10                  15

Ala Lys (2) INFORMATION FOR SEQ ID NO:12:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Arg Ala Leu Val Asp Thr Glu Phe Lys Val Lys Gln Glu Ala Gly Ala
   1               5                  10                  15

Lys (2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Tyr Arg Ala Leu Val Asp Thr Leu Lys Phe Val Thr Gln Ala Glu Gly
   1               5                  10                  15

Ala Lys (2) INFORMATION FOR SEQ ID NO:14:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO:14:

Val Gly Val Ala Pro Gly Val Gly Val Ala Pro Gly Val Gly Val Ala
1               5                   10                  15

Pro Gly (2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Position 1 is either
            unprotected or protected with a formyl group."

(xi) SEQUENCE DESCRIPTION: SEQ ID NO:15:

Asn Leu Leu Phe Asn Leu Tyr Lys
1               5

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Val Pro Gly Val Gly Val Pro Gly Val Gly Val Pro Gly Val Gly Val
1               5                   10                  15

Pro Gly Val Gly
            20

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Position 1 is either
            unprotected or protected with a formyl group."

(xi) SEQUENCE DESCRIPTION: SEQ ID NO:17:

Met Ile Phe Leu
1

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: linear

```
       (ii) MOLECULE TYPE: peptide (ix) FEATURE:
            (A) NAME/KEY: Modified-site
            (B) LOCATION: 1
            (D) OTHER INFORMATION: /note= "Position 1 is either
                unprotected or protected with a formyl group."

(xi) SEQUENCE DESCRIPTION: SEQ ID NO:18:

Met Leu Phe Lys
   1

(2) INFORMATION FOR SEQ ID NO:19:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Position 1 is either
                unprotected or protected with a formyl group."

(xi) SEQUENCE DESCRIPTION: SEQ ID NO:19:

Met Leu Phe Ile
   1

(2) INFORMATION FOR SEQ ID NO:20:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Position 1 is either
                unprotected or protected with a formyl group."

(xi) SEQUENCE DESCRIPTION: SEQ ID NO:20:

Met Phe Ile Leu
   1

(2) INFORMATION FOR SEQ ID NO:21:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Position 1 is either
                unprotected or protected with a formyl group."

(xi) SEQUENCE DESCRIPTION: SEQ ID NO:21:

Met Phe Leu Ile
   1
```

(2) INFORMATION FOR SEQ ID NO:22:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Position 1 is either
            unprotected or protected with a formyl group."

(xi) SEQUENCE DESCRIPTION: SEQ ID NO:22:

Met Leu Ile Phe
   1

(2) INFORMATION FOR SEQ ID NO:23:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Position 1 is either
            unprotected or protected with a formyl group."

(xi) SEQUENCE DESCRIPTION: SEQ ID NO:23:

Met Ile Leu Phe
   1

(2) INFORMATION FOR SEQ ID NO:24:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Position 1 is either
            unprotected or protected with a formyl group."

(xi) SEQUENCE DESCRIPTION: SEQ ID NO:24:

Thr Lys Pro Arg
   1

(2) INFORMATION FOR SEQ ID NO:25:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide

```
        (xi) SEQUENCE DESCRIPTION: SEQ ID NO:25:

Val Gly Val Ala Pro Gly
    1               5

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

Tyr Ile Gly Ser Arg
    1               5

(2) INFORMATION FOR SEQ ID NO:27:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Position 1 has a CH2CO
            substituent."

(xi) SEQUENCE DESCRIPTION: SEQ ID NO:27:

Tyr Ile Gly Ser Arg Cys
    1               5

(2) INFORMATION FOR SEQ ID NO:28:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Asn Asp Gly Asp Phe Glu Glu Ile Pro Glu Glu Tyr Leu Gln
    1               5                   10

(2) INFORMATION FOR SEQ ID NO:29:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /note= "Position 12 has a SO3Na
            substituent"
```

(xi) SEQUENCE DESCRIPTION: SEQ ID NO:29:

Asn Asp Gly Asp Phe Glu Glu Ile Pro Glu Glu Tyr Leu Gln
    1               5                   10

(2) INFORMATION FOR SEQ ID NO:30:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Gly Pro Arg Gly
    1

(2) INFORMATION FOR SEQ ID NO:31:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Asp Phe Pro Arg Pro Gly Gly Gly Asn Gly Asp Phe Glu Glu Ile
    1               5                   10                  15

Pro Glu Glu Tyr Leu
                20

(2) INFORMATION FOR SEQ ID NO:32:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Arg Arg Arg Arg Arg Arg Arg Arg Arg Gly Asp Val
    1               5                   10

(2) INFORMATION FOR SEQ ID NO:33:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Pro Leu Tyr Lys Lys Ile Ile Lys Lys Leu Leu Glu Ser
    1               5                   10

(2) INFORMATION FOR SEQ ID NO:34:

(i) SEQUENCE CHARACTERISTICS:
        (A) LENGTH: 4 amino acids
        (B) TYPE: amino acid (C) STRANDEDNESS: single
          (D) TOPOLOGY: linear (ii) MOLECULE TYPE: peptide (xi) SEQUENCE DESCRIPTION: SEQ ID NO:34:

Arg Gly Asp Ser
    1

(2) INFORMATION FOR SEQ ID NO:35:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:35:

Glu Lys Pro Leu Gln Asn Phe Thr Leu Ser Phe Arg
    1               5                  10

(2) INFORMATION FOR SEQ ID NO:36:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:36:

Thr Lys Pro Pro Arg
    1               5

(2) INFORMATION FOR SEQ ID NO:37:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: 6
          (D) OTHER INFORMATION: /note= "Position 6 has an -OH
             substituent."

(xi) SEQUENCE DESCRIPTION: SEQ ID NO:37:

Gly Thr Lys Pro Pro Arg
    1               5

(2) INFORMATION FOR SEQ ID NO:38:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Modified-site
          (B) LOCATION: 1

```
        (D) OTHER INFORMATION: /note= "Position 1 has an
            N,N-dimethyl substituent."

(ix) FEATURE:
        (A) NAME/KEY: Modified-site
        (B) LOCATION: 9
        (D) OTHER INFORMATION: /note= "Position 9 is either
            unsubstituted or has an -OH substituent."

(xi) SEQUENCE DESCRIPTION: SEQ ID NO:38:

Gly Thr Cys Gly Thr Lys Pro Pro Arg
    1               5

(2) INFORMATION FOR SEQ ID NO:39:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Position 1 has a sarcosine
            substituent."

(xi) SEQUENCE DESCRIPTION: SEQ ID NO:39:

Ser Cys Gly Thr Lys Pro Pro Arg
    1               5
```